US012685482B2

(12) United States Patent
Lemmens et al.

(10) Patent No.: US 12,685,482 B2
(45) Date of Patent: Jul. 21, 2026

(54) SLEEP MEDICAMENT DISPENSING SYSTEM

(71) Applicant: KONINKLIJKE PHILIPS N.V., Eindhoven (NL)

(72) Inventors: Paul Marcel Carl Lemmens, Veghel (NL); Timmy Robertus Maria Leufkens, Upplands Väsby (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 592 days.

(21) Appl. No.: 18/025,047

(22) PCT Filed: Sep. 8, 2021

(86) PCT No.: PCT/EP2021/074627
§ 371 (c)(1),
(2) Date: Mar. 7, 2023

(87) PCT Pub. No.: WO2022/053470
PCT Pub. Date: Mar. 17, 2022

(65) Prior Publication Data
US 2023/0320937 A1     Oct. 12, 2023

(30) Foreign Application Priority Data
Sep. 9, 2020     (EP) .................................... 20195181

(51) Int. Cl.
*A61B 5/00*          (2006.01)
*A61J 7/00*          (2006.01)
(Continued)

(52) U.S. Cl.
CPC .......... *A61B 5/4815* (2013.01); *A61B 5/4839* (2013.01); *A61J 7/0076* (2013.01);
(Continued)

(58) Field of Classification Search
CPC ... A61B 5/4815; A61B 5/4839; A61B 5/4812; A61B 5/4806; A61B 5/4809;
(Continued)

(56) References Cited

U.S. PATENT DOCUMENTS 8,055,348 B2 * 11/2011 Heruth ................... G16H 40/63
607/45
9,474,876 B1 * 10/2016 Kahn ................... A61B 5/4812
(Continued)

FOREIGN PATENT DOCUMENTS

| WO | WO-2019014717 A1 * | 1/2019 | ......... A61B 5/02405 |
| WO | WO-2019067781 A1 * | 4/2019 | ........... A61N 5/0618 |
| WO | 2020081761 A1 | 4/2020 | |

OTHER PUBLICATIONS

International Search report and Written Opinion of PCT/EP2021/074627, dated Nov. 11, 2021.

*Primary Examiner* — Wesley G Harris
(74) *Attorney, Agent, or Firm* — Brynne J. Corcoran

(57)     ABSTRACT

A sleep medication dispensing system is for controlling release of a sleep medicament to a user based on sleep information related to the user. The system includes an electronic medicament dispensing device with a release mechanism to permit release of a controlled dose of a sleep medication which is stored in a holding area of the device. The system includes a processing arrangement which receives the user sleep pattern information, and performs a release assessment which depends at least in part on the sleep pattern information. Release of a dose of the sleep medication in a given instance is made dependent upon an outcome of the release assessment.

11 Claims, 4 Drawing Sheets

(51) Int. Cl.
   *A61J 7/04*          (2006.01)
   *G16H 20/13*        (2018.01)
   *G16H 40/63*        (2018.01)

(52) U.S. Cl.
   CPC ........... *A61J 7/0418* (2015.05); *A61J 7/0481*
           (2013.01); *G16H 20/13* (2018.01); *G16H*
           *40/63* (2018.01); *A61B 5/4857* (2013.01);
           *A61J 2200/30* (2013.01); *A61J 2200/70*
                                  (2013.01)

(58) Field of Classification Search
   CPC ...... A61J 7/0076; A61J 7/0418; A61J 7/0481;
           A61J 2200/30; A61J 2200/70; G16H
               20/13; G16H 40/63; A61M 21/02
   See application file for complete search history.

(56)                References Cited

U.S. PATENT DOCUMENTS

| | | | |
|---|---|---|---|
| 2009/0192556 A1* | 7/2009 | Wu ........................ | A61B 5/1116 |
| | | | 607/3 |
| 2014/0277822 A1* | 9/2014 | Nunn ................... | A47C 27/083 |
| | | | 700/301 |
| 2017/0246086 A1* | 8/2017 | Jain ...................... | A61B 5/4833 |
| 2017/0319815 A1 | 11/2017 | Nofzinger et al. | |
| 2018/0333558 A1 | 11/2018 | Levendowski et al. | |
| 2019/0224445 A1 | 7/2019 | Fernandes et al. | |
| 2019/0236465 A1 | 8/2019 | Vleugels et al. | |
| 2021/0378916 A1* | 12/2021 | Shalon ................. | A61J 7/0418 |

* cited by examiner

Sleep Quality

Mon  Tue  Wed  Thu  Fri  Sat  Sun  Mon  Tue  Wed  Thu  Fri

SLEEP MEDICAMENT DISPENSING SYSTEM

CROSS-REFERENCE TO PRIOR APPLICATIONS

This application is the U.S. National Phase application under 35 U.S.C. § 371 of International Application No. PCT/EP2021/074627, filed on Sep. 8, 2021, which claims the benefit of European Patent Application No. 20195181.1, filed on Sep. 9, 2020. These applications are hereby incorporated by reference herein.

FIELD OF THE INVENTION

This invention relates to an electronic sleep medicament dispensing system.

BACKGROUND OF THE INVENTION

Hypnotics (sleep medication or sleeping pills) are used in the treatment of insomnia, and include prescription medications and also over-the-counter sleeping pills. Prescription by doctors is based on generic treatment regimes. As a consequence, individuals using hypnotics may begin to use the medications chronically. Alternatively, in the cases where prescription is for occasional, intermittent use, a patient may use the drug too often and during nights where a sleeping aid is not necessary. This can lead to variety of adverse effects including increased tolerance to the medication (due to habituation of use), daytime sleepiness, and problems with addiction or withdrawal.

The lack of personalization of prescription of the drug may compound these problems.

These adverse effects may require further treatment to bring the patient to recovery, e.g. counselling to taper off the medication.

An improved means for administering sleeping medication to a patient which may at least partially mitigate the above problems would be desirable.

WO2020/081761A1 discloses a dispensing system including a handheld dispenser and a dispenser controller. The handheld dispenser may have a housing, a cartridge removably disposed within the housing and containing a dose form to be dispensed, the dose form with an active pharmaceutical ingredient (API), the cartridge having an internal piston movable within a reservoir containing the dose form and a port through a distal tip in communication with the reservoir, the distal tip being sized and configured to be inserted into the user's mouth. The dispenser controller adjusts the volume of the dose form dispensed by the dispenser based on information about effectiveness of the API in treating a condition of the user.

SUMMARY OF THE INVENTION

The invention is defined by the claims.

According to examples in accordance with an aspect of the invention, there is provided a medicament dispensing system for dispensing sleep medication, comprising: an electronic dispensing device comprising one or more medicament holding areas being electronically releasable to dispense a controlled dose of medicament; and a processing arrangement, operatively coupled to the dispensing device. The processing arrangement is adapted to: receive sleep pattern information related to a user from a local or remote source; and control release of a medicament dose dependent upon an outcome of a release assessment, the release assessment being based at least in part on the user sleep pattern information.

Embodiments of the present invention are based on regulating administration of a sleeping medication to a patient in a way that is personalized to their sleeping habits. A processing arrangement of the system communicates with a source of sleep information for the user and uses this to decide, on a case-by-case basis, whether a dose of the sleeping medicament is needed on a given occasion. For example, the processing arrangement can check whether the user has been sleeping badly in the preceding one or more nights and, if so, may release the medication. On the contrary, if the subject is sleeping well, a dose may not be released. More sophisticated examples of analyzing the sleep pattern information will be discussed later. Thus, in effect, a personalized medication administration regime can be implemented, tailored directly to the sleeping patterns of the user, and these can be kept up to date in real time based on sleep tracking information for the user for example. This can help to avoid overuse of the medicament, since it should only be administered when sleep patterns indicate it would be of benefit clinically.

The system may include a communication interface for receiving the user sleep pattern information. It may be received from an external datastore or system for example. Alternatively, it may be received from a local data source.

The processing arrangement may be adapted to release access to the medicament in release events, each release event comprising: receiving a user release request signal (e.g. from a user interface or user control element); performing the release assessment; and releasing a controlled dose of medicament dependent upon a positive result of the assessment.

Thus a release event is in the first instance initiated by a user seeking a dose of the sleep medication. The release assessment may check whether the dose is needed, based at least on the user sleep pattern information or information derived therefrom.

The controller may be operable to control a dose of the medicament, or the dose may be standard and fixed.

The request signal may be received from a portable computing device in some examples.

The user sleep pattern information may be indicative of patterns in one or more properties of the user's sleep over time.

In a simplest case, it may comprise a representation of a time series of historical values. The pattern information may comprise a representation of the variation in the sleep property as a function of time, a representation of trends over time, a function representing a curve of the property values over time, and/or may comprise statistical information about the user's sleep properties (e.g. average or modal value of a given sleep property).

The properties of the user's sleep may include sleep quantity and/or a measure of sleep quality. Sleep quantity may mean a temporal duration of sleep in a single defined unit time (e.g. one night or one full day (24 hours)). Sleep quality can be based on properties such as, but not limited to: sleep-onset latency, number of awakenings after sleep onset, length of wake-ups during sleep (known in the field as Wake After Sleep Onset (WASO, in minutes)), level of movement during sleep, relative duration of the different levels of sleep during a sleep period (e.g. REM, light sleep, deep sleep etc.), Total Sleep Time, Total Time in Bed and Sleep Efficiency.

The received sleep pattern information may comprise information representative of historical patterns in the one or more properties of the user's sleep and/or predicted or projected future sleep pattern information for the user. The predicted future pattern information can be derived based on historical pattern information. In some examples, the processing arrangement may derive the predicted future sleep pattern information from received historical pattern information. In other examples, the predicted future pattern information may be received as the input sleep pattern information at the processing arrangement.

The processing arrangement may be adapted to generate a predicted value or measure for one or more properties of the user's sleep for a future sleep session based on the received user sleep pattern information. This may be done based on interpolating from trends present in the received sleep pattern information for example. The future sleep session may mean the temporally next (upcoming) sleep session.

A positive outcome for the release assessment may require meeting at least one release criterion related to the generated predicted value or measure. For example, a release criterion may include that the generated predicted value or measure is above or below a defined threshold.

The received sleep pattern information may comprise information indicative of a historical cyclical pattern in one or more sleep properties over a time scale, and wherein the release assessment is based on estimating a current point or phase within the temporal cycle of that cyclical pattern.

For example, the sleep pattern information may show that a user tends to sleep well on one set of days of the week (e.g. the weekend), and badly in the other set of days (e.g. weekdays).

Upon receipt of a release request, the medication release can be dependent upon a current point in this cycle at which the request signal is being received. The medication may be dispensed if in a part of the cycle associated with sleep below a defined threshold for a given property for example, and not if in a part of the cycle associated with sleep above the defined threshold for quality or quantity (or vice versa).

This temporal cycle may be identified by the processing arrangement from the received sleep pattern data, or an indication of the cycle may be included as part of the received sleep pattern information.

In examples, the cyclical pattern may be represented in the form of a function, representing a sleep property as a function of time. Other possibilities will be apparent.

The release assessment may comprise determining a first or second order trend in the cyclical pattern at said estimated current point or phase in the temporal cycle. A trend may mean a gradient or derivative.

Determining a trend may comprise determining a derivative of the cyclical pattern. The cyclical pattern might be represented by a function or by a time-series of data values, and a derivative can be calculated analytically or numerically respectively in these cases.

In some examples, determining the trend may comprise determining whether a second order derivative or trend of a sleep property (such as sleep quality or sleep quantity) as a function of time is negative (at a time point in the trend corresponding to a current time point). This has predictive capability as it indicates that the sleep property, according to the cyclical pattern, is due to soon deteriorate (reduce in value).

In accordance with one or more embodiments, the processing arrangement may be adapted to access (from a local or remote source) a (personalized) predictive sleep model for the user, having parameters configured based on historical patterns in user sleep properties, and wherein the received sleep pattern information is information derived from the predictive sleep model. The model may embody cyclical trends in sleep properties for example.

In accordance with one or more embodiments, the processing arrangement may be adapted to log a time of each successful release event in a datastore. The log can be used in tracking medicament use which data can be used in diagnostic monitoring and also as part of subsequent release assessments.

For example, the release assessment may additionally be based on a history of previous release events in the log. This can help to avert overuse and habituation. For example, a user may be prevented from taking doses too close to one another, or too many doses in a certain time period (e.g. a week), or may have a maximum allowed number of successive days on which doses are released.

In accordance with one or more embodiments, the release assessment may be additionally based on an elimination half-life of the medicament dispensed.

For example, it may be based on estimating a remaining amount of the medicament in the body of the user based on the elimination half-life and the log of release events. This can further help prevent over-exposure of the user to the drug, thus helping to prevent habituation and/or tolerance.

The processing arrangement may be further adapted to detect changes in one or more properties of a user's sleep following a release event and to modify or update sleep pattern information based on the detected changes.

For example, it might update parameters of a predictive sleep model for the user.

This feature aims at determining an effect of a medicament on sleep properties of a user and updating the sleep pattern information accordingly.

In accordance with one or more embodiments, the processing arrangement may further comprise an override function triggered responsive to receipt of a pre-defined override signal, and wherein, in the override function, the release assessment is overridden. For example, release of a dose of the medicament may be directly triggered.

In examples, the override signal may be a signal received from a secure authentication device, e.g. a pin code entry device.

In accordance with one or more embodiments, the medicament dispensing system may additionally include a sleep monitoring arrangement adapted to acquire sleep tracking information for the user, for use in determining one or more properties of the user's sleep.

The sleep monitoring arrangement may generate the sleep pattern information related to the user based on the acquired sleep tracking information.

Examples in accordance with a further aspect of the invention provide a computer-implemented method of controlling dispensing of sleep medication using an electronic dispensing device comprising one or more medicament holding areas being electronically releasable to dispense a controlled dose of medicament. The method comprises: obtaining sleep pattern information related to a user; and controlling release of medicament doses from the dispensing device dependent upon an outcome of a release assessment, the release assessment being based at least in part on the received user sleep pattern information.

In accordance with one or more embodiments, the processing arrangement may be integrated in the electronic dispensing device so that they form a single unit.

Examples in accordance with a further aspect of the invention provide a computer program product comprising computer program code, the computer program code being executable on a processor or computer wherein, when the processor or computer is operatively coupled with an electronic dispensing device comprising one or more medicament holding areas being electronically releasable to dispense a controlled dose of medicament, the code is configured to cause the processor to perform a method in in accordance with any example or embodiment outlined above or described below, or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying schematic drawings, in which.

DETAILED DESCRIPTION OF THE EMBODIMENTS

Figure 1:
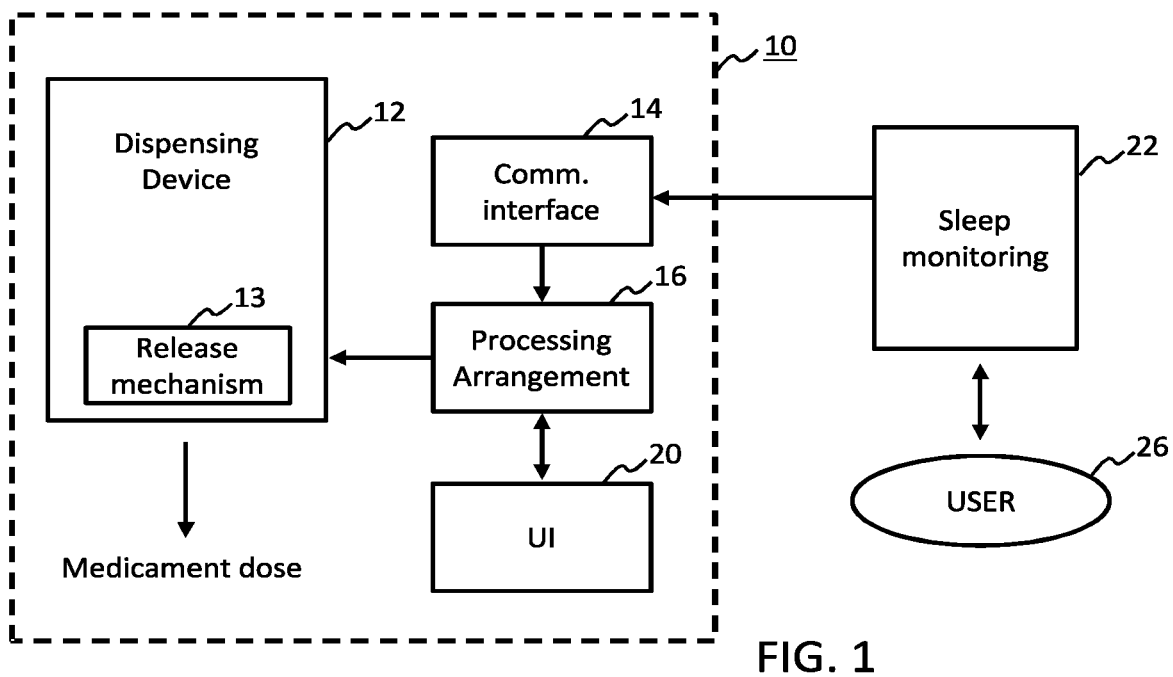
FIG. 1 shows components of an example medicament dispensing system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a sleep medication dispensing system for controlling release of a sleep medicament to a user based on sleep information related to the user. The system includes an electronic medicament dispensing device with a release mechanism to permit release of a controlled dose of a sleep medication which is stored in at least one holding area of the device. The system includes a processing arrangement which receives the user sleep pattern information, and performs a release assessment which depends at least in part on the sleep pattern information. Release of a dose of the sleep medication in a given instance is made dependent upon an outcome of the release assessment.

FIG. 1 outlines components of an example medicament dispensing system 10 for dispensing sleep medication, some of or all of which components may be included in different embodiments, as will be explained.

The system includes an electronic dispensing device 12 comprising one or more medicament holding areas being electronically releasable to dispense a controlled dose of medicament. The device for example includes a release mechanism 13 which can be triggered with a release trigger signal to cause release of a controlled dose of the medicament from a holding area.

The system further includes a processing arrangement 16, operatively coupled to the dispensing device. It may be integrated in the dispensing device in some examples so that the two are comprised by a single unit.

The processing arrangement 16 is adapted to receive sleep pattern information related to a user from a local or remote source. In the example of FIG. 1, the system further includes an optional communication interface 14 for receiving for receiving the user sleep pattern information from an external source (meaning a source outside of the dispensing system 10). In such examples, the sleep pattern information may in general be received from any external datastore. Alternatively, the information be received from a local datastore, in which case a communication interface may not be needed for receiving the data.

In the example of FIG. 1, the information is received from a sleep monitoring arrangement which is arranged for monitoring sleep properties of a user 26, and deriving sleep pattern information for the user based thereon. This derived sleep pattern information may be stored in a datastore comprised by the sleep monitoring arrangement. The sleep monitoring arrangement may be a distributed system, for example comprising a sleep tracking device, e.g. a wearable unit, which is used to acquire sleep tracking data of the user 26. It may include a processing component which processes the sleep tracking data to acquire the sleep pattern information, and the processing component may or may not be embodied in a separate unit to the tracking device. For example, it may be embodied in a portable computing device such as a smartphone which connects with the sleep tracking device. The arrangement may include a datastore which stores the sleep pattern information, which datastore may or may not be embodied in a same unit as the processing component. For example in some cases, the data may be stored in cloud-based storage resource. The communication interface 14 of the dispensing system 10 may communicate with a datastore component of the sleep monitoring arrangement. Alternatively it may communicate with a processing component of the sleep monitoring arrangement, which may act as a hub or portal to provide access to the stored sleep pattern data, e.g. a Smartphone connects to the dispensing system and communicates stored data which the smartphone retrieves from a remote datastore.

The sleep monitoring arrangement 22 may be comprised as part of the dispensing system 10 provided by the present invention, but in general it is anticipated that the sleep monitoring arrangement is a separate system with which the claimed system 10 merely communicates.

The communication interface 14 is preferably a wireless communication interface. It may comprise a chip or a card comprising communication components according to one or more communication modes or protocols, e.g. Bluetooth, Wi-Fi, ZigBee, wireless LAN, wired LAN, USB or any other format. The communication interface may be an Internet-based connection interface, receiving data via connection to one or more host Web addresses.

The processing arrangement 16 is operatively coupled with the communication interface 14. The processing arrangement is adapted to control release of a medicament dose dependent upon an outcome of a release assessment 36, the release assessment being based at least in part on user sleep pattern information. Controlling release of a medicament dose may comprise transmitting a release trigger signal to the release mechanism 13 of the dispensing device. Options for controlled release of medicament doses will be further explained later.

The system may include a user interface 20 including a user input means for receiving user control signals or commands, and preferably a sensory user output means. The user interface may be used by the user to request release of a dose of medication. It may include a physical or digital button which, upon user actuation, triggers transmission of a user release request signal to the processing arrangement 16.

In general, the processing arrangement may be adapted to release access to the medicament in (discrete) release events, each release event comprising: receiving a user release request signal (e.g. from the user interface 20); performing the release assessment; and releasing a controlled dose of medicament dependent upon a positive result of the assessment.

Figure 2:
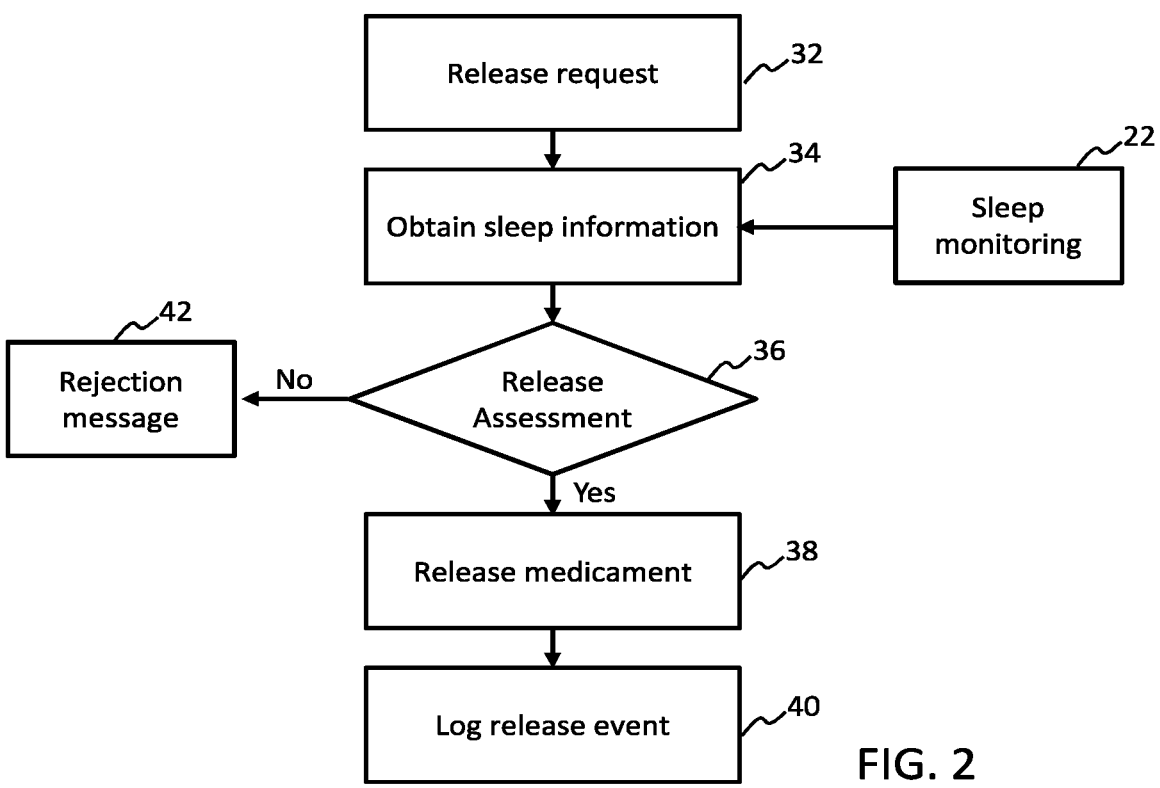
FIG. 2 shows an example processing workflow corresponding to a medicament a release event.

An example workflow for a release event is outlined schematically in FIG. 2. Initially a user actuates generation of a release request signal 32, which is received by the processing arrangement 16. The processing arrangement obtains 34 sleep information for the user, for example from a sleep monitoring arrangement 22, but alternatively from any other source. This step may already have been performed in advance of the release request signal. For example, the system 10 may continuously update a local cache of sleep pattern information for a user by means of the communication module. In either event, a release assessment 36 is performed after the sleep pattern data has been acquired.

With regards to the release assessment 36, this may in general comprise one or more algorithms which may be stored on a local datastore of the processing arrangement 16 or may be encoded in the programming or operation of the processing arrangement. The release assessment may be associated with a set of release criteria defining conditions which must be met for release of a dose of the medicament to be performed. The release criteria may be encoded in the processing arrangement, or may be stored in a local or remote datastore and retrievable by the processing arrangement. The release criteria may be fixed in advance, or they may be adjustable or configurable. The release criteria include at least one criterion which is related to properties of the user sleep pattern information.

The release assessment 36 may comprise determining whether each of the one or more release criteria has been met. Dependent upon the result of these one or more determinations, the release assessment may have a positive outcome or may have a negative outcome. If the release assessment has a positive outcome, the processing arrangement 16 is adapted to trigger release of a controlled dose of the medicament held by the electronic dispenser device 12. If the release assessment is negative, the processing arrangement does not trigger release of the medicament. Optionally, a sensory output may be generated 42 by means of a user interface device 20 to advise the user of the negative outcome. A reason may be given as part of the sensory output, for example an indication of the release criterion which was not met.

A positive outcome of the release assessment may require all of the one or more release criteria to be met, or may require only a subset to be met, or may require any one of the criteria to be met. At least the (at least one) criterion related to the user sleeping patterns must be met. The release criteria may each be tagged in advance as to whether its meeting is essential or not essential to a positive outcome of a release assessment.

If the release assessment has a positive outcome, a time-stamped record of the release event may be stored in a data log 40. Optionally a dose which was released in the release event may also be stored in the log. The log may be held in a local or a remote datastore. The history of release events in the log may be used as part of subsequent release assessments as will be explained further later.

In general, the sleep pattern information relates to patterns or variations over time in one or more properties of a user's sleep. The properties may include for example sleep quality and sleep quantity. Sleep quantity may mean a temporal duration of sleep in a single defined unit time (e.g. one night or one full day (24 hours)). Sleep quality can be defined in different ways but in general is determinable based on properties such as, but not limited to: sleep-onset latency, number of awakenings after sleep onset, length of wake-ups during sleep (known in the field as Wake After Sleep Onset (WASO, in minutes)), level of movement during sleep, relative duration of the different levels of sleep during a sleep period (e.g. REM, light sleep, deep sleep etc.), Total Sleep Time, Total Time in Bed and Sleep Efficiency.

It is anticipated that in general the sleep pattern information may be compiled by an external sleep monitoring arrangement or system 22. The sleep monitoring arrangement may be comprised as part of the system provided by the present invention, or may be a separate system with which the claimed system merely communicates. The sleep monitoring arrangement may determine the sleep properties for a given sleep session based on acquired sleep tracking data for that session. The sleep monitoring arrangement may include a sleep tracking device or arrangement, for example a wearable device. For example, a wearable device with a movement sensor may be used to acquire user movement data during user sleep. The movement data may be the sleep tracking data. The sleep monitoring arrangement may include processing hardware, local or remote, for processing the sleep tracking information and determining the one or more sleep properties pertaining for the sleep session based on the sleep tracking data. The processing hardware may be embodied on a mobile computing device with which the sleep tracking device operatively connected, e.g. a Smartphone of the user.

The derived sleep properties for each sleep session may be recorded, either on a local datastore of a device comprised by the sleep monitoring arrangement, or in a remote datastore, such as cloud-based datastore. Over time, a historical dataset or record of user sleep properties is compiled, with derived properties for different sleep sessions recorded, and time-stamped according to the time and date of the sleep session.

From this personalized historical sleep dataset for the user, patterns in each of the one or more sleep properties over time may be identified, inferred or extracted. These may be periodic or cyclical (temporal) variations or trends in the properties over time in some examples. In other cases, patterns may refer to statistical information about the sleep properties over a given time scale, e.g. a minimum and maximum value (a range), a variability, or a modal or median value of one or more of the properties. The patterns may correspond to trends in the properties in some examples.

Different patterns may be identifiable over different classes of time scale such as short term, mid-term and long-term. Each of these classes of time scale may correspond to a defined minimum and/or maximum window of time preceding a current time. For example, considering data over only a very short term (e.g. a few days), it is unlikely that cyclical variations in properties of sleep such as sleep quality or quantity will be observable. However, there may be observable patterns in the form of statistical information such as a maximum/minimum value of the sleep properties, a range of the sleep properties, or an average or modal value of the sleep properties. These statistical properties may form short-term sleep pattern information. There may also be discernable trends in the properties, e.g. sleep quality improving over the last few days or sleep quality deteriorating, which may also form part of short-term sleep pattern information.

Over the medium or long term, cyclical variations in the sleep properties may be identifiable, e.g. over the course of a single week, or month or year. Multiple different cyclical patterns over different time scales may be superposed atop one another, for example a seasonal variation in sleep quality (e.g. poorer quality sleep in summer, and better quality sleep in winter), with a more mid-term variation/fluctuation superposed atop that (e.g. over the course of a single week, e.g. on weekdays a user has poorer quality sleep, while at weekends has better quality sleep).

The sleep monitoring arrangement may analyze the compiled historical sleep dataset for the user and identify patterns in the sleep properties over different classes of time period, and thus compile sleep pattern information for the user indicative or based on this.

From the historical patterns in the sleep properties, predictions or projections of estimated future sleep properties may be generated. For example if a sleep pattern comprises a long term (seasonal) cyclical variation in sleep patterns, a predicted value of a sleep property may be predicted based on identifying a point or phase in the cycle which corresponds to current time point. Additionally or alternatively, the long term pattern may be analyzed to identify an estimated trend in one or more sleep properties corresponding to the current time point. From this, a prediction or projection may be made as to sleep properties in the corning night (or other upcoming sleep session).

If only short term historical sleep data is available, derivable patterns may correspond only to an average, modal value or range of values for a given sleep property. This information may be used to generate a prediction as to estimated sleep properties in the coming sleep session. The short term data may include a pattern indicative of a short term trend. This trend can be projected forwards, and an estimated value for the sleep properties in the coming sleep session estimated.

In general, the sleep pattern information received at the communication interface and the processing arrangement may comprise data representative of historical pattern information observable in the historical patient sleep data (over any one or more classes of time-scale), and/or may comprise predictive sleep pattern information representative of a predicted or projected future trend (or other pattern) in the sleep properties of the user over a certain time window. The predictive sleep pattern information may be generated by the sleep monitoring arrangement 22, or by the processing arrangement 16 of the dispensing system in different examples. In either of these cases, the processing arrangement is adapted to use the received information in the release assessment 36.

Figure 3:
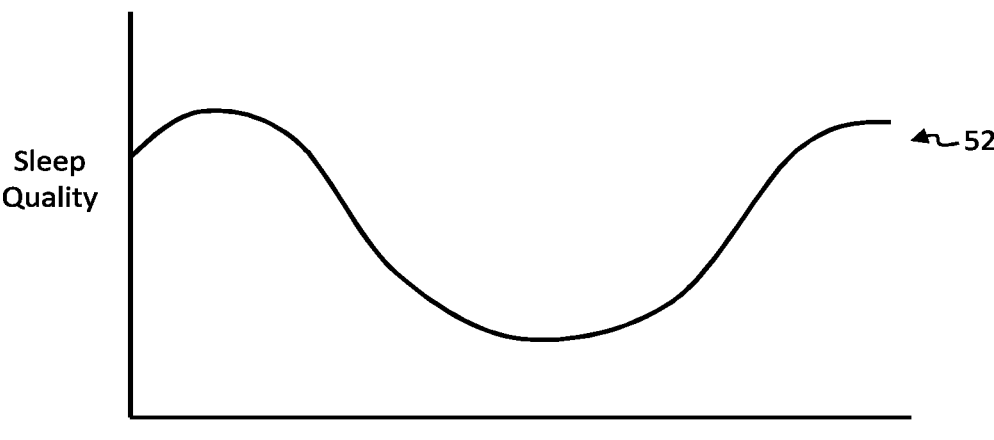
FIGS. 3-5 show example sleep pattern information in the form of a long-term cyclical trend in a sleep property.

One example is shown in FIG. 3 which shows sleep pattern information 52 in form of a historical cyclical pattern in sleep quality for a user over a time period of a whole year. This temporal cycle may be identified by the processing arrangement from the received sleep data, or an indication of the cycle may form the received sleep pattern information. It can be seen that a user's sleep quality tends to improve in winter, and then deteriorate over summer.

Figure 4:
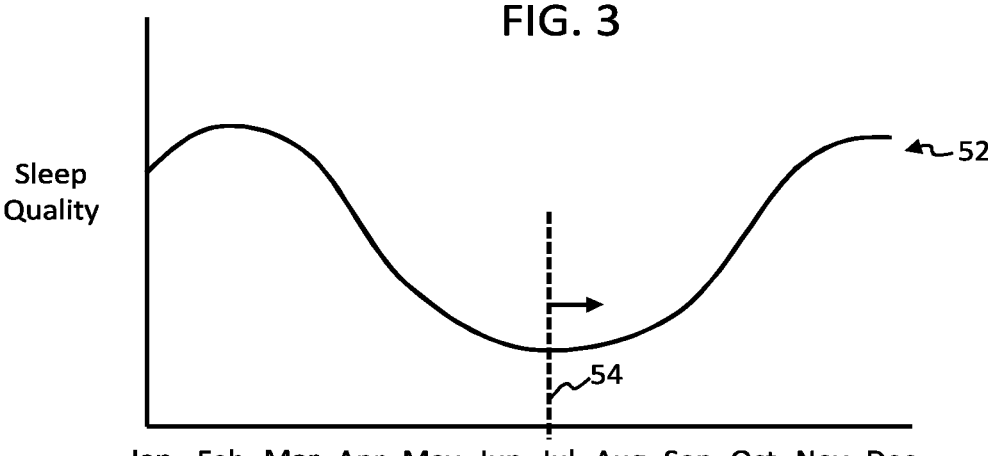

The release assessment 36 may be based on estimating a current point or phase within the temporal cycle. This is illustrated in FIG. 4, where the processing arrangement has identified the point in the cycle corresponding to the current time 54 (i.e. the time at which a release request has been received). Based on this, the processing arrangement may estimate what a current sleep quality of the user may be, as the sleep quality value of the pattern 52 coinciding with the current time point and/or may estimate how the user's sleep quality may progress in the future, based on how the cyclical pattern 52 progresses (i.e. a trend of the cyclical pattern at the time point corresponding to the current time point).

For example, in some cases, the processing arrangement 16 may further process received sleep pattern information 52 to derive a projected or predicted future trend, or a predicted future value of one or more sleep properties, and wherein the release assessment includes a release criterion dependent upon this result, for example a threshold. Additionally or alternatively, the processing arrangement may comprise an algorithm which is configured to receive as an input the received sleep pattern information (in one of the formats discussed above for example) and to derive a value of a *sui generis* metric, a value of which metric is directly used in the release assessment.

For example, in one set of embodiments, the release assessment 36 may comprise the processing arrangement 16 generating a predicted value or measure for one or more properties of the user's sleep (e.g. sleep quantity and/or quality) for a next upcoming sleep session based on received sleep pattern information.

This may be done based on interpolating or projecting forward from trends present in the received sleep pattern information 52 for example.

For example, and with reference to FIG. 4, if the sleep pattern information comprises information indicative of a historical cyclical pattern in one or more sleep properties over a time scale (as discussed above), it may be based on determining a current point or phase within the temporal cycle of that cyclical pattern, and interpolating forwards based on the trend. For example, in FIG. 4, the current time point is at the bottom of a valley in the curve, and the cycle indicates that sleep quality may be about to improve. Thus, the processing arrangement may estimate that a sleep quality value of the user in the upcoming sleep session may be slightly higher than was observed by the sleep monitoring arrangement during the previous sessions.

A positive outcome of the release assessment may be dependent upon the generated predicted value or measure for the one or more properties of the user's sleep for the next sleep session meeting a defined threshold, e.g. falling below a threshold for predicted sleep quality and/or quantity. If the threshold for the predicted sleep property for the upcoming night is met, the medicament dose is released.

In one or more examples, The release assessment may comprise determining a first or second order trend in the cyclical pattern 52 at said estimated current point 54 or phase in the temporal cycle. Determining a trend may comprise determining a derivative of the cyclical pattern. The cyclical pattern might be represented by a function or by a time-series of data values, and a derivative can be calculated analytically or numerically respectively in these cases.

In some examples, determining the trend may comprise determining whether a second order derivative or trend of a sleep property (such as sleep quality or sleep quantity) as a function of time is negative. This has predictive capability as it indicates that the sleep property, according to the cyclical pattern, is due to soon deteriorate (reduce in value).

Figure 5:
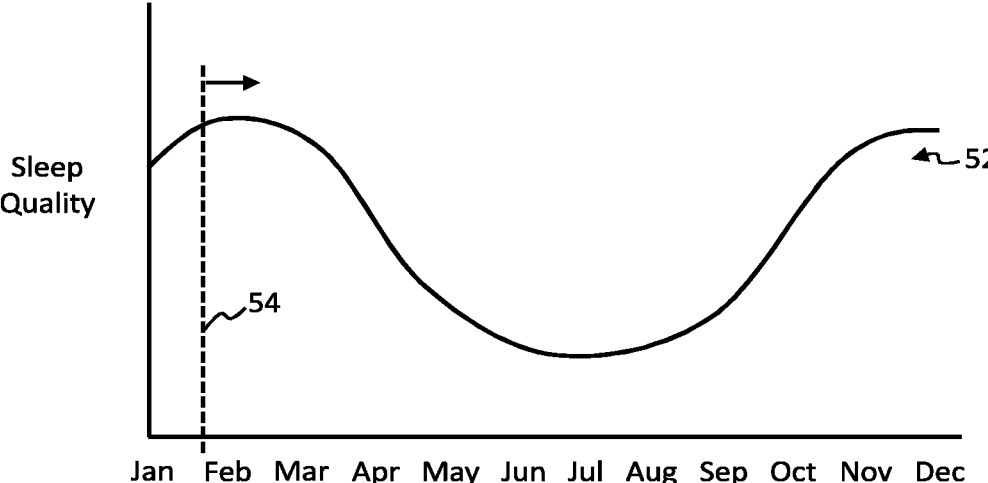

This is illustrated in FIG. 5 which shows that a current time point 54 corresponds to a point on the cyclical pattern 52 of sleep quality which is approaching a peak. At this point, the first order trend is positive (positive gradient), but the second order trend (e.g. second order derivative) is negative because the first order slope is declining with time. The processing arrangement may identify that the current time point corresponds to a point in the cycle with a negative second order gradient, and may use this to predict that user sleep quality may soon begin to decline. In the release assessment, this may lead to a positive outcome of a release request since sleep medication may help to offset the upcoming expected decline in the user's sleep quality.

Figure 6:
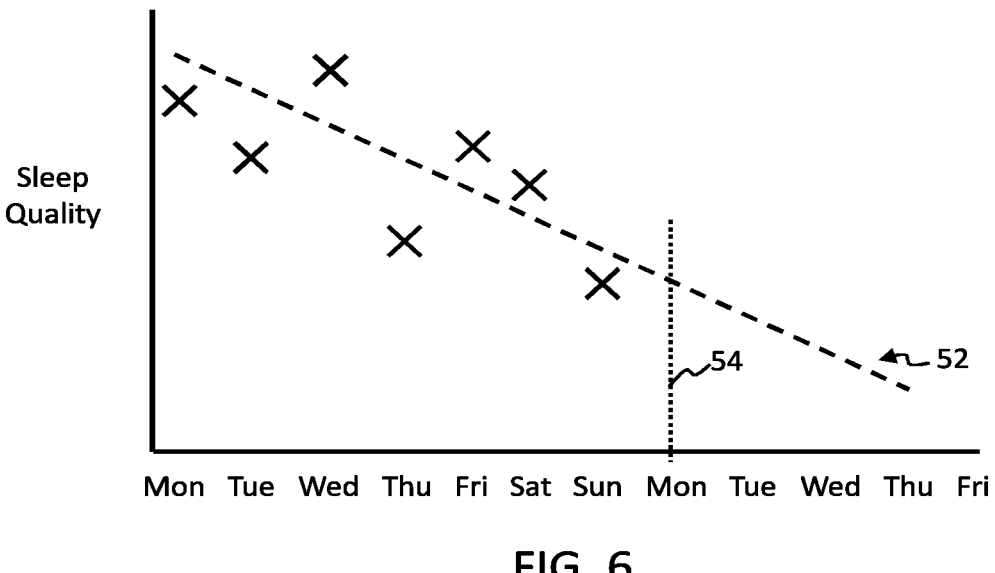
FIG. 6 shows a further example of sleep pattern information in the form of a short-term trend in a sleep property.

FIG. 6 shows a further example. In this case, the sleep pattern information 52 takes the form of a short term trend in values of a sleep property of the user. In particular, the pattern corresponds to a trend in sleep quality values for the subject over a time scale of one week preceding a current time point 54. From this, a negative trend in the sleep quality values has been identified, for example by the sleep monitoring arrangement 22. Alternatively, the processing arrangement may derive the trend. The trend can be projected forward to provide predictive future pattern information for the sleep quality. For example, based on the trend, the processing arrangement may predict that a sleep quality will be lower in an upcoming sleep session than in the last sleep session. This may be used in the release assessment to estimate whether a user will need a dose of sleep medication for the upcoming sleep session.

Although the example of FIG. 6 shows determining a linear trend (e.g. by linear regression) based on the pattern of sleep quality values, this is by way of one example only. In further examples, other types of trends may additionally or alternatively be derived such as non-linear trends or polynomial trends. The skilled person will be aware of standard statistical techniques for deriving a variety of different types of trends from data.

In some examples, historical pattern information can be used to construct a personalized predictive sleep model for a user, having parameters configured based on historical patterns in user sleep properties. For example, the predictive sleep model may comprise a compilation or superposition of multiple different patterns or trends observable in historical user sleep data over multiple different time scales, and wherein this combined pattern information forms a model for how user sleep properties may progress with time at any given time point. In some examples, the received sleep pattern information may be information derived from the predictive sleep model. The predictive sleep model may be generated by the sleep monitoring arrangement 22 for example and stored on a datastore thereof.

As discussed above, following a successful release event, optionally the processing arrangement may be is adapted to log a time of the release event in a datastore. The datastore may be local or remote to the processing arrangement. A successful release event means that the outcome of the release assessment was to release a dose of the medicament.

Each release assessment 36 may additionally be based on a history of previous release events in the log.

In some examples, the release assessment may additionally be based on an elimination half-life of the medicament dispensed. This information may be received from a local reference datastore for instance. For instance, a doctor may input this information via the user interface when configuring the dispensing system. Alternatively, the information may be received via a communication interface from a remote source, e.g. an internet web address.

The release assessment for example may comprise estimating a remaining amount of the medicament in the body of the user based on the elimination half-life and the log of release events. This may be determined for example from the timings of the previous release events, and a dosage of medicament released each time, and the half-life of the medicament. A positive outcome of a release assessment may be made dependent upon this determined amount of medicament remaining the body being below a pre-defined minimum threshold.

For example, the threshold may be set so that release of a new dose is dependent upon the medicament being substantially cleared from the body (e.g. at least 80% cleared, e.g. at least 90% cleared).

In some embodiments, the medicament half-life and dosage information may be used in combination with the sleep pattern information to determine an outcome of a release assessment. For example, if a certain sleeping pill promotes sleep onset latency, has a half-life of 12 hours, and the user took the pill during the night, during the next evening, the user's body may still have sufficient active agent available to promote sleep onset only if the seasonal model predicts above average scores for sleep quality and quantity. In this case, the release of a sleeping medicament can be blocked. Otherwise, release of a sleeping medicament may be triggered.

In accordance with one or more embodiments, the processing arrangement may be adapted to detect changes in one or more properties of a user's sleep following a release event and to modify or update sleep pattern information based on the detected changes.

The historical sleep pattern information over a relative longer time period may be modified or modulated based on short term changes in sleep properties detected responsive to release of one or more doses. In other words, the longer term (e.g. seasonal) patterns can be adjusted based on an assumption that the medicament will continue to be taken. This can assist in managing administration of the sleep dose over time.

For example following a release event, and after the next sleep session has ended, the processing arrangement may determine (automatically or using manual input) the effect of a medicament dose on sleep quality and sleep quantity. Based on this assessment the sleep pattern information may be updated. For example, a personalized sleep pattern model may be updated, or cyclical pattern data may be updated. This can be done for instance using standard statistical techniques such as adding parameters to the model and using these parameters to adjust the models predictions. Other methods to adjust the seasonal patterns for the effect of the sleeping pill are also possible. This adjustment can also be done on an ongoing basis, even when no medicament has been administered.

Additionally or alternatively, the processing arrangement 16 may be adapted to modify parameters (e.g. thresholds) of the release criteria used in the release assessment based on the detected changes in the sleep properties.

In accordance with one or more embodiments, the processing arrangement may comprise an override function triggered responsive to receipt of a pre-defined override signal, and wherein in the override function, the release assessment is overridden. Release of a dose of the medicament may be directly triggered responsive to receipt of both the override signal and a user request signal. In examples, the override signal may be a signal received from a secure authentication device, e.g. a pin code entry device, or a biometric authentication device such as a fingerprint scanner. This allows an authorized person, such as a doctor, to override the restricted release functionality of the processing arrangement. As another example, a doctor might grant a user a temporary override code which they can enter on a single occasion to override the restrictions of the release assessment. As another example, a certain defined number of override events may be permitted within a given time window and may be triggered by a user actuating a dedicated user control. In further examples, the patient or user (e.g. relative or caregiver) might also be an authorized person who can authorize override.

In accordance with one or more embodiments, the processing arrangement may comprise a medicament tapering assistance function, wherein the release criteria used in the release assessment may include one or more criteria configured to enforce a gradual decrease in usage of the sleep medicament by the user. This may be based on criteria which refer to entries in the release event log, and enforce a restriction on the number of doses which may be taken in a given unit time. This maximum allowed number of doses in that unit time may be controlled to gradually reduce over time so that a user is gradually tapered off of the medication, or tapered down to a lower intake level. The additional tapering-related release criteria are applied in addition to the at least one criterion which is based on the user sleep pattern information. Hence a user might be predicted poor quality sleep for an upcoming night, but is denied a dose of the sleep medicament because the tapering requirements mean they have already taken the maximum number of doses in the defined time window (e.g. 1 week).

Embodiments include an electronic dispensing device which holds the medicament and is adapted to release the medicament in controlled dose release events. There are a wide variety of different options for the structure and configuration of the dispensing device. In general the electronic dispensing device should include a release mechanism 13 which allows release of a single dose of a stored medicament at a time, responsive to receipt at the mechanism of a defined trigger signal, and wherein release of a dose means that the dose is moved from a position in which it is located in a part of the device which is physically inaccessible to a user (e.g. in a locked chamber), to a part of the device which is physically accessible to a user. A dose may comprise a single capsule or tablet for example. However other dispensing arrangements may also be considered, such as arrangements for dispensing controlled doses of a liquid medicament e.g. through an actuable valve.

By way of one non-limiting example, the dispensing device may comprise a rotary carrousel comprising an annular array of separate chambers, each forming a respective medicament holding area for holding a single dose of the medicament. The chambers may be in the form of trays which are open across the top. The carrousel may mounted in rotatable configuration within an outer housing. The outer housing may comprise a roof portion which covers the carousel and physically blocks access to the medicament holding areas. The annular array of chambers map onto a corresponding annular area of the roof portion above, and wherein the roof portion may comprise an access window at one location within this annular area. The access window may comprise an opening through the roof portion, of a size which matches, or is smaller than, the open area over the top of each respective medicament holding tray or chamber. One of the holding areas may be aligned with the window at any one time, and wherein, when aligned, access is provided to the area via the window. Release of a controlled dose of the medicament may comprise electronically indexing a rotary positon of the carousel to progressively expose different holding chambers to the open window.

Instead of a window, there may be a drop zone, and wherein alignment of a holding chamber with the drop zone causes gravitational release of the held medicament, whereupon it may enter a holding tray accessible to a user.

The device may include an actuation mechanism for driving the rotation of the rotary carrousel. This actuation mechanism may form the release mechanism 13 in this example, and may be adapted to actuate a rotatory indexing of the carrousel responsive to receipt of a release signal from the processing arrangement.

In another example, the electronic dispensing device could have a gravity column design, wherein the device comprises a single holding chamber arranged to hold a plurality of different doses of the medicament (e.g. a plurality of capsules or pills). At a base of the chamber may be a release mechanism actuable to permit controlled drop through the base of the chamber of a single dose at a time, and wherein a dispensing tray is mounted beneath the drop area and accessible to the user. The release mechanism may be a controllable trapdoor for example or a tipping mechanism.

The above represent examples presented for the purpose of illustration only and a wide variety of other suitable examples will be apparent to the skilled person.

There are different options for the architecture of the system.

Figure 7:
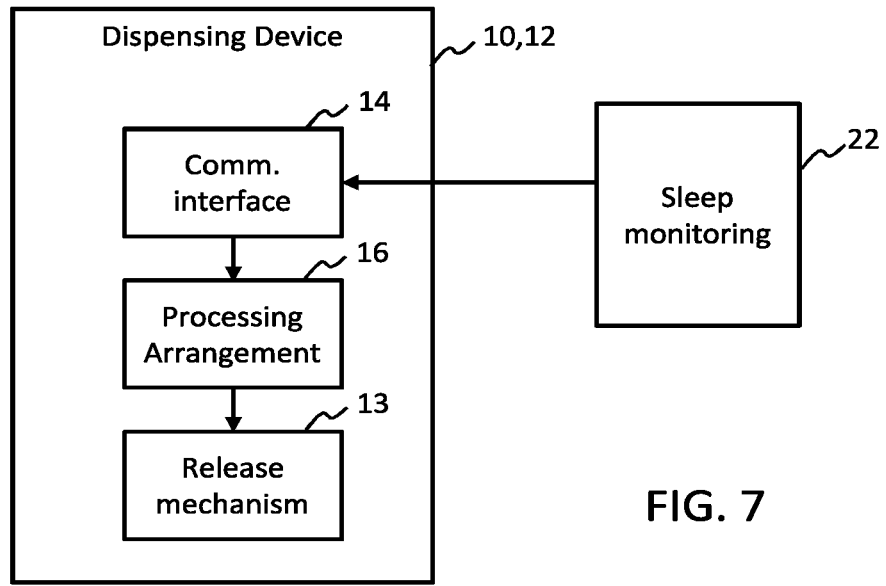
FIG. 7 shows one example architecture for a system according to one or more embodiments, in which the processing arrangement is integrated in the dispensing device.

As schematically illustrated in FIG. 7, the processing arrangement 16 may be integrated in the electronic dispensing device 12, such that the two form a single unit. In this instance, the dispensing device itself forms the dispensing system 10. The processing arrangement 16 may receive the sleep pattern information from a data source either internal to the sensing device (e.g. stored on a local datastore within the dispensing device), or from an external source, such as from a sleep monitoring arrangement 22 (as shown in FIG. 7 and discussed above).

Figure 8:
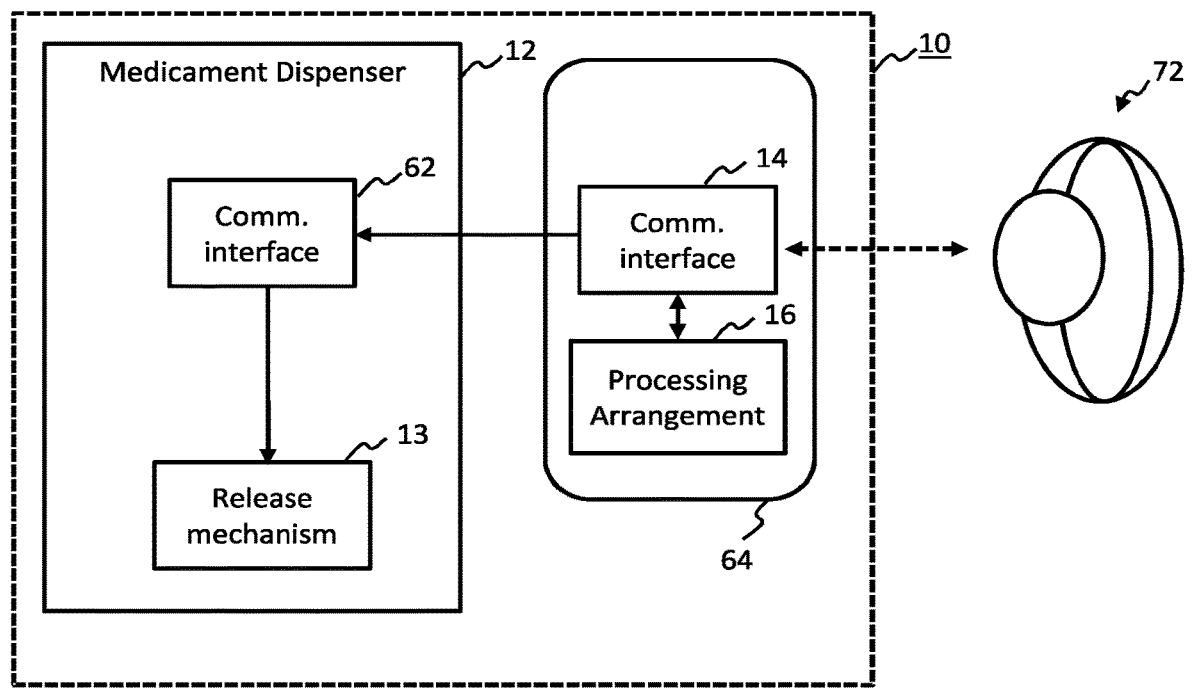
FIG. 8 shows a further example architecture for a system according to one or more embodiments, in which the processing arrangement is external to the dispensing device, integrated in a portable computing device.

In a further option, the dispensing system 10 may be a distributed system, in which the processing arrangement 16 is located in a different unit or structure from the electronic dispensing device 12. One example is shown in FIG. 8. In this example, the processing arrangement 16 is embodied within the hardware of a portable computing device 64. For example it might be provided by the local processing components of the portable computing device itself. The portable computing device may be a smartphone or tablet computer for example. The processing arrangement 16 is provided coupled to a communication interface 14 which may be a native communication interface of the portable computing device 64 in some examples. The processing arrangement controls release of medicament doses from the dispenser device 12 via issuing control instructions, e.g. a release trigger signal, which are transmitted to the dispenser device 12 via the communication interface. The dispenser device includes a local communication interface 62 which is arranged to receive the control instructions and to transfer them to a release mechanism 13 for triggering release of a controlled dose of the medicament.

The sleep pattern information in this example may be stored on a local datastore of the personal computing device 64. Alternatively it may be stored in a remote datastore, for example a cloud-based datastore, and wherein the processing arrangement 16 is arranged to receive the sleep pattern information via the communication interface 14.

Optionally, the personal computing device may also form part of a sleep monitoring arrangement. For example, it may be communicatively coupled or paired with a user sleep tracking device 72, such as a wrist-wearable activity tracker, as illustrated in FIG. 8. This may acquire sleep tracking data, from which a local processor of the portable computing device 64 may derive sleep pattern information, which may be stored on the computing device or uploaded to an external datastore.

Examples in accordance with a further aspect of the invention provide a computer-implemented method of controlling dispensing of sleep medication using an electronic dispensing device comprising one or more medicament holding areas being electronically releasable to dispense a controlled dose of medicament. The method comprises: obtaining sleep pattern information related to a user; and controlling release of medicament doses from the dispensing device dependent upon an outcome of a release assessment, the release assessment being based at least in part on the received user sleep pattern information.

Examples in accordance with a further aspect of the invention provide a computer program product comprising computer program code, the computer program code being executable on a processor or computer wherein, when the processor or computer is operatively coupled with an electronic dispensing device comprising one or more medicament holding areas being electronically releasable to dispense a controlled dose of medicament, the code is configured to cause the processor to perform a method in in accordance with any example or embodiment outlined above or described below, or in accordance with any claim of this application.

Embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A medicament dispensing system for dispensing sleep medication, comprising:
    an electronic dispensing device comprising one or more medicament holding areas being electronically releasable to dispense a controlled dose of medicament;
    a processing arrangement, operatively coupled to the dispensing device, and adapted to: receive sleep pattern information related to a user from a local or remote source
        wherein the user sleep pattern information is indicative of patterns in one or more properties of the user's sleep over time and wherein the received sleep pattern information comprises information representative of historical patterns in the one or more properties of the user's sleep and/or projected future sleep pattern information for the user, and comprises information indicative of a historical cyclical pattern in one or more sleep properties over a time scale;
    generate a predicted value or measure for one or more properties of the user's sleep for a future sleep session based on the received user sleep pattern information;
    and control release of a medicament dependent upon an outcome of a release assessment, the release assessment being based at least in part on the predicted value or measure, and based on estimating a current point or phase within the temporal cycle of the cyclical pattern, and comprising determining a first or second order derivative of the cyclical pattern as a function of time at said estimated current point or phase in the temporal cycle.

2. The system as claimed in claim 1, wherein the processing arrangement is adapted to control release of the medicament in release events, each release event comprising:

receiving a user release request signal;

performing the release assessment;

releasing the controlled dose of medicament dependent upon a positive result of the assessment.

3. The system as claimed in claim 2, wherein the processing arrangement is adapted to log a time of each successful release event in a datastore, and wherein the release assessment is additionally based on a history of previous release events in the log.

4. The system as claimed in claim 3, wherein the release assessment is additionally based on an elimination half-life of the medicament dispensed and optionally based on estimating a remaining amount of the medicament in the body of the user based on the elimination half-life and the log of release events.

5. The system as claimed in claim 1, wherein the properties of the user's sleep include sleep quantity and/or a measure of sleep quality.

6. The system as claimed in claim 1, wherein the processing arrangement is arranged to access a personalized predictive sleep model for the user, having parameters configured based on historical patterns in user sleep properties, and wherein the received sleep pattern information is information derived from the predictive sleep model.

7. The system as claimed in claim 6, wherein the processing arrangement is adapted to detect changes in one or more properties of a user's sleep following a release event and to modify or update sleep pattern information based on the detected changes.

8. The system as claimed in claim 1, wherein the processing arrangement further comprises an override function triggered responsive to receipt of a pre-defined override signal, and wherein in the override function, the release assessment is overridden and release of a dose of the medicament is directly triggered.

9. The system as claimed in claim 1, further comprising a sleep monitoring arrangement adapted to acquire sleep tracking information for the user, for use in determining one or more properties of the user's sleep.

10. A computer-implemented method of controlling dispensing of sleep medication using an electronic dispensing device comprising one or more medicament holding areas being electronically releasable to dispense a controlled dose of medicament; the method comprising:

obtaining sleep pattern information related to a user wherein the user sleep pattern information is indicative of patterns in one or more properties of the user's sleep over time and comprises information representative of historical patterns in the one or more properties of the user's sleep and/or projected future sleep pattern information for the user, and comprises information indicative of a historical cyclical pattern in one or more sleep properties over a time scale; generating a predicted value or measure for one or more properties of the user's sleep for a future sleep session based on the obtained user sleep pattern information;

and controlling release of a medicament dependent upon an outcome of a release assessment, the release assessment being based at least in part on the predicted value or measure, and based on estimating a current point or phase within the temporal cycle of the cyclical pattern, and comprising determining a first or second order derivative of the cyclical pattern as a function of time at said estimated current point or phase in the temporal cycle.

11. A computer program product comprising: computer program code, the computer program code being executable on a processor or computer wherein, when the processor or computer is operatively coupled with an electronic dispensing device comprising one or more medicament holding areas being electronically releasable to dispense a controlled dose of medicament, the code is configured to cause the processor or computer to perform the method in accordance with claim 10.

\*   \*   \*   \*   \*